've
United States Patent [19]

Swartz

[11] 4,273,638

[45] Jun. 16, 1981

[54] ELECTROCHEMICAL SENSING PROBE

[75] Inventor: Dorian J. Swartz, Yorba Linda, Calif.

[73] Assignee: American Hospital Supply Corporation, Evanston, Ill.

[21] Appl. No.: 142,488

[22] Filed: Apr. 21, 1980

Related U.S. Application Data

[63] Continuation of Ser. No. 970,890, Dec. 19, 1978, abandoned.

[51] Int. Cl.³ ............................................. G01N 27/54
[52] U.S. Cl. .................................................. 204/195 P
[58] Field of Search ............................. 204/195 P, 1 P

[56] References Cited

U.S. PATENT DOCUMENTS

| | | | |
|---|---|---|---|
| 3,351,544 | 11/1967 | Medlar | 204/195 P |
| 3,454,485 | 7/1969 | Hauk et al. | 204/195 P |
| 3,468,781 | 9/1969 | Lucero | 204/195 P |
| 3,476,672 | 11/1969 | Snyder et al. | 204/195 |
| 3,510,421 | 5/1970 | Gealt | 204/195 P |
| 3,518,179 | 6/1970 | Bleak et al. | 204/195 P |
| 3,676,220 | 7/1972 | Ward | 204/195 P X |
| 3,785,948 | 1/1974 | Hitchman et al. | 204/195 P |
| 3,826,730 | 7/1974 | Watanabe et al. | 204/195 P |
| 3,875,037 | 4/1975 | Krull | 204/195 P |
| 3,886,058 | 5/1975 | Barna | 204/195 P |
| 4,078,981 | 3/1978 | Neti et al. | 204/195 P |

*Primary Examiner*—G. L. Kaplan
*Attorney, Agent, or Firm*—Larry N. Barger

[57] ABSTRACT

A probe for monitoring the gas concentration, such as oxygen in an anesthesia respiratory therapy circuit, which includes a reusable connector and conductive coupling structure to a sealed housing containing an electrolyte and two electrodes in contact with the electrolyte. The sealed housing has a gas sensing port closed off by a selectively pervious membrane.

23 Claims, 4 Drawing Figures

ELECTROCHEMICAL SENSING PROBE

This is a continuation of application Ser. No. 970,890 filed Dec. 19, 1978, now abandoned.

BACKGROUND

Gas sensing probes have been known which include the selectively pervious gas membrane closing the gas sensing port of an electrolyte housing that also includes a cathode and an anode extending into the electrolyte. Such sensing probes are frequently used to monitor the level of oxygen in anesthesia equipment. U.S. Pat. Nos. 3,351,544 and 3,826,730 describe the general background use of such sensing probes in which a cathode is placed very close to a membrane that is selectively pervious to the gas being tested. The gas passing the membrane into the electrolyte chamber participates in an electrochemical reaction manifested by an electric current flow between polarized electrodes. The current varies as a function of the gas's partial pressure and can therefore measure its concentration.

In the past, these sensing probes have had very short lives and had to be reconstructed quite often because the anode became corroded or the spacing between the cathode and membrane, which might be as small as 0.001 inch, became clogged or altered. Thus, there was a problem in cleaning or replacing the cathode and adding new electrolyte and membrane substructures to these sensors. U.S. Pat. No. 3,351,544 required a complicated dismantling of the electrolyte chamber to change the cathode and membrane.

U.S. Pat. No. 3,826,730 discloses a reusable connector with a long depending anode that is pushed through a top opening in a disposable electrolyte housing. Cathode connection between the reusable connector and the electrolyte housing is made through a conductive screw.

The probe described in U.S. Pat. No. 3,826,730 had very serious shortcomings in that its storage and useful life was very short. Such probes carried a warning to use before a certain date, specified as 3 months after shipment. The reason for this short life was the dehydration and/or contamination of the electrolyte. The electrolyte was in a form of a gel, but during assembly of the reusable connector and disposable electrolyte housing the seams were not always air-tight, and could permit the electrolyte to evaporate over a period of time from the orifice through which the anode extended into the electrolyte chamber of the disposable housing.

A different type probe is described in U.S. Pat. No. 3,476,672 which uses a single electrode in a half cell for sensing the ion concentrations in solutions, such as a pH meter. Such a cell with a single electrode in the electrolyte would be inoperative for sensing gas concentrations which require an electrolyte with both a cathode and an anode in contact with the electrolyte.

SUMMARY OF THE INVENTION

The above problems, such as the short life span and electrolyte loss described above, have been overcome with the present invention. This invention includes a sealed housing which contains therein an electrolyte and two electrodes in contact with the electrolyte, and there are conductive members extending through a wall of the sealed housing for connecting the electrodes to separate leads. In a preferred embodiment, the electrolyte housing has an anode that is adhesively bonded to the housing and protrudes through the housing providing a stub for coupling to a conductive socket in a reusable connector. Since the electrolyte housing is completely sealed, there is no chance of loss of electrolyte through a reception opening for a protruding anode from the reusable connector. Alternate coupling structures between the disposable electrolyte housing and the reusable connector are described.

THE DRAWINGS

DETAILED DESCRIPTION

Figure 1:
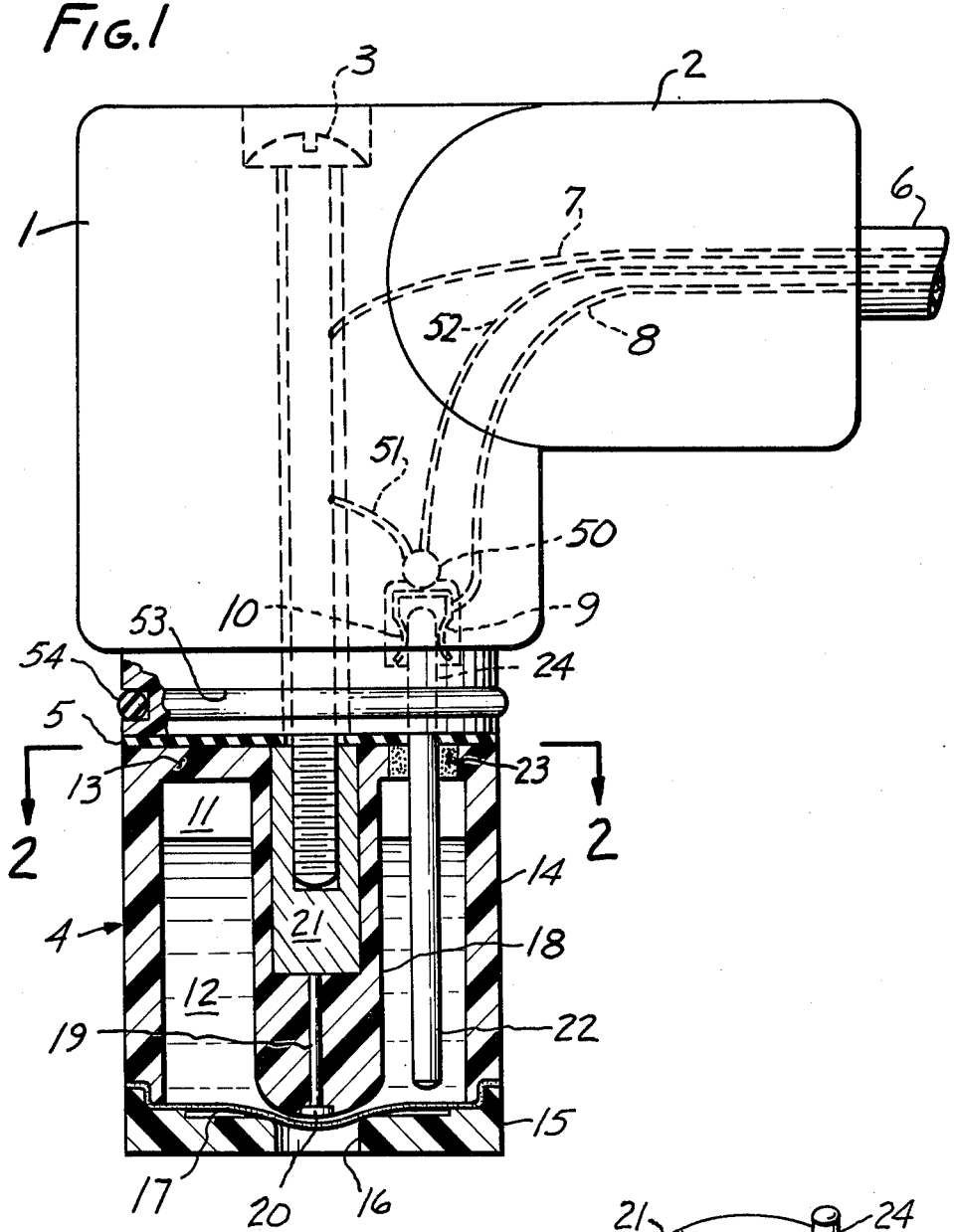
FIG. 1 is a side elevational view of the sensing probe with the sealed disposable electrolyte housing shown in sections.

FIG. 1 shows the sensing probe which includes a reusable connector 1 that can include an integral sidearm 2. A conductive screw fastener 3 secures the reusable connector to a disposable electrolyte housing 4. Preferably, a sealing gasket 5 is used at the juncture. A groove 53 includes O-ring 54 for sealing the sensing probe in a tubular arm of a T-coupling (not shown) that carries the gas to be sensed.

Connector 1 has joined to its sidearm 2 an electrical cord 6 that can lead to an electrical metering device (not shown) for monitoring a particular gas concentration, such as in an anesthesia or respiratory therapy circuit. Cord 6 includes leads 7 and 8 which respectively couple to conductive screw 3 and an electrically conductive socket 9 that preferably includes an internal spring clip 10. A thermister 50 with leads 51 and 52 can be used to compensate for temperature variations, if desired.

The electrolyte housing 4 is preferably of a thermoplastic material and includes an annular chamber 11 that is substantially filled with electrolyte 12 which can be in gel form. The different types of electrolytes are well-known to those skilled in the art and forms no part of the present invention. The electrolyte housing 4 includes a top wall 13 and a depending side wall 14 that terminates at a bottom edge. The cap 15 is secured to the side wall 14 and includes a gas sensing port 16. A membrane 17 is sealed between the housing's wall 14 and in cap 15 so that it fans and closes off gas sensing port 16 from an interior of the electrolyte housing. Membrane 17 is selectively pervious to the particular gas being tested, such as oxygen.

A central post section 18 depends from an upper wall 13 of the housing and encases a cathode 19 that can have an enlarged contact button 20, if desired. Alternatively, cathode 19 can be a straight cylindrical wire of a material such as gold. Center post 18 includes a cavity into which is embedded an internally threaded conductive socket 21 of a material such as brass. Screw 3 is threadingly received in socket 21 and tightening of screw 3 pulls housing 4 and connector 1 into firm connection with each other. Through screw 3 and socket 21, lead 7 is electrically connected to cathode 19.

Anode 22 is adhesively bonded to the housing's top wall 13 at 23, and includes a stub portion 24 received in socket 9. Thus, it can be seen that lead 6 is electrically connected to cathode 22 through spring contact 10 of socket 9. Anode 22 is offset from screw 3 to prevent rotation of the electrolyte housing relative to the connector 1 when screw 3 is turned for assembly and disassembly. Also, the stub portion 24 permits the user to push the housing into the socket 9 to hold both units firmly together while actuating the screw.

The button end 20 of cathode 19 is in very close proximity to the membrane 17, such as 0.001 inch. However, the contact is not so close that all electrolyte is squeezed out of contact with button 20. One way to insure contact of cathode button 20 with the electrolyte is to roughen the ends of post 18 and cathode button 20 to provide minute passages for electrolyte to come in contact with button 20. Thus, it can be seen that both the cathode 19 with its button 20 and anode 22 are both in contact with the same electrolyte. It is desirable to maintain button 20 as close as possible to membrane 17 so that it can accurately sense the changes of the gas to be measured migrating across the membrane 17.

Figure 2:
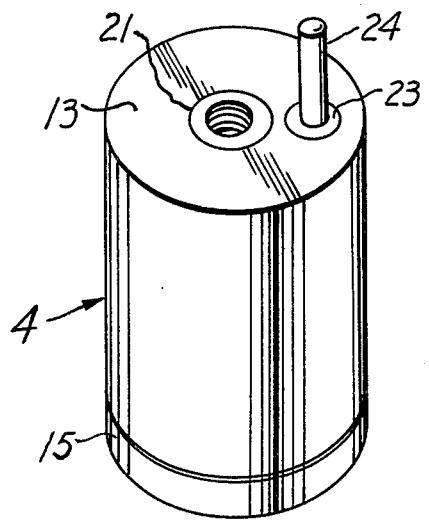
FIG. 2 is a top perspective view of the sealed electrolyte housing.

FIG. 2 shows the disposable sealed electrolyte housing 4 with its protruding anode stub 24 and threaded socket 21 visible from a top wall 13 of the housing. As the disposable electrolyte housing shown in FIG. 2 has no openings through which the electrolyte can evaporate, such housing can last several times longer in storage and use than a housing with an open port through which an anode on the reusable connector can be inserted in the manner described in U.S. Pat. No. 3,826,730.

Figure 3:
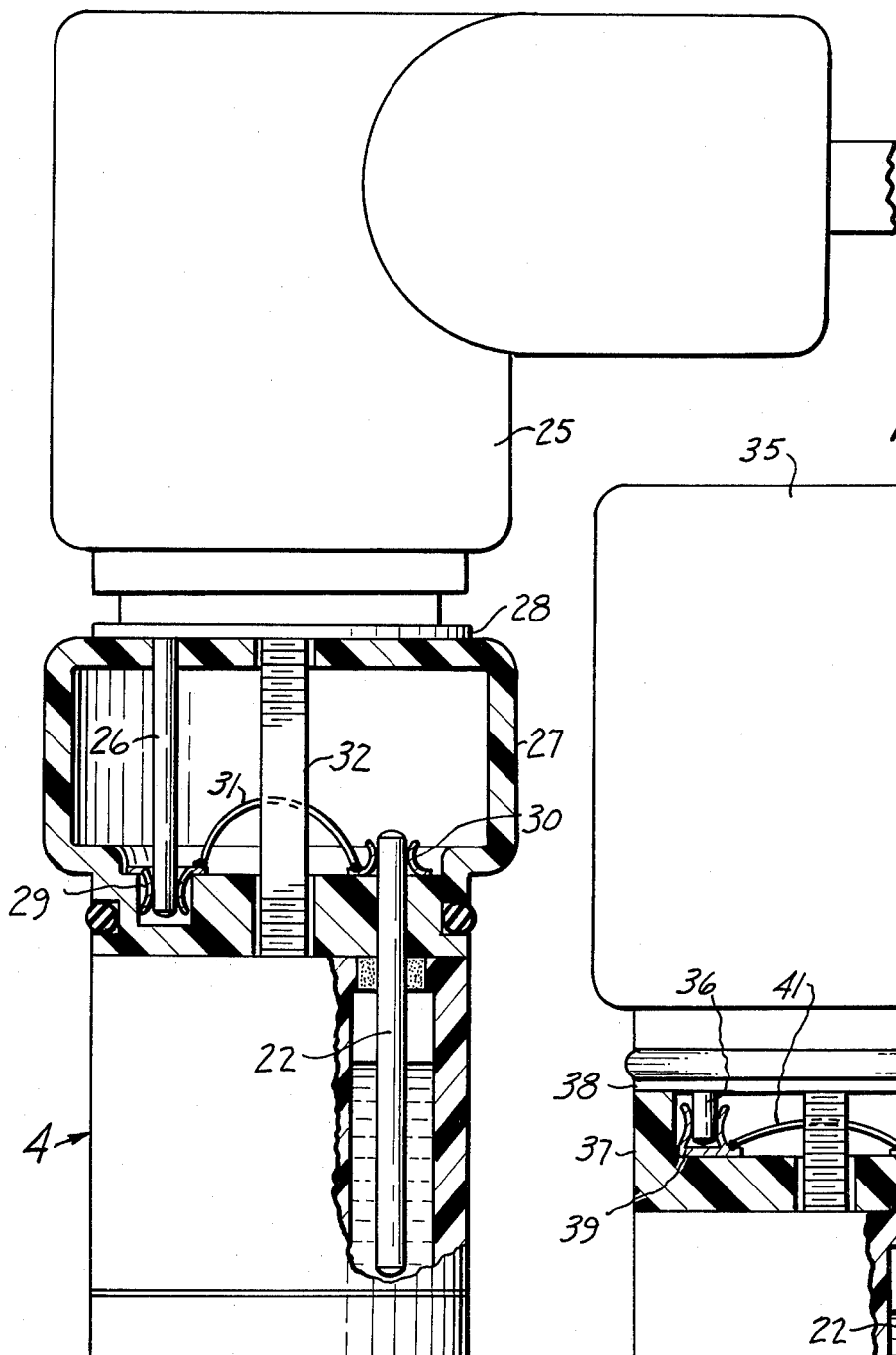
FIG. 3 is a sectional view of the sealed electrolyte housing joined to a reusable connector by means of a hollow spacer which receives a protruding anode of the reusable connector.

FIG. 3 shows the electrolyte housing 4 which is identical to that shown in FIGS. 1 and 2 coupled to a reusable connector 25 that has a long depending anode 26, such as was used to dip into an electrolyte in a housing that had an open hole for receiving anode 26. In FIG. 3, there is a hollow spacer 27 that fits between a gasket 28 and electrolyte housing 4. A pair of offset spring clip sockets 29 and 30 are electrically connected by wire 31 so that anode 26 of connector 5 is in electrical contact with anode 22 of the disposable electrolyte chamber. Anode 26 and anode 22 are not coaxial as shown in FIG. 3. To compensate for the length of spacer 27, a screw 32 is provided that is significantly longer than the screw 3 of FIG. 1.

Figure 4:
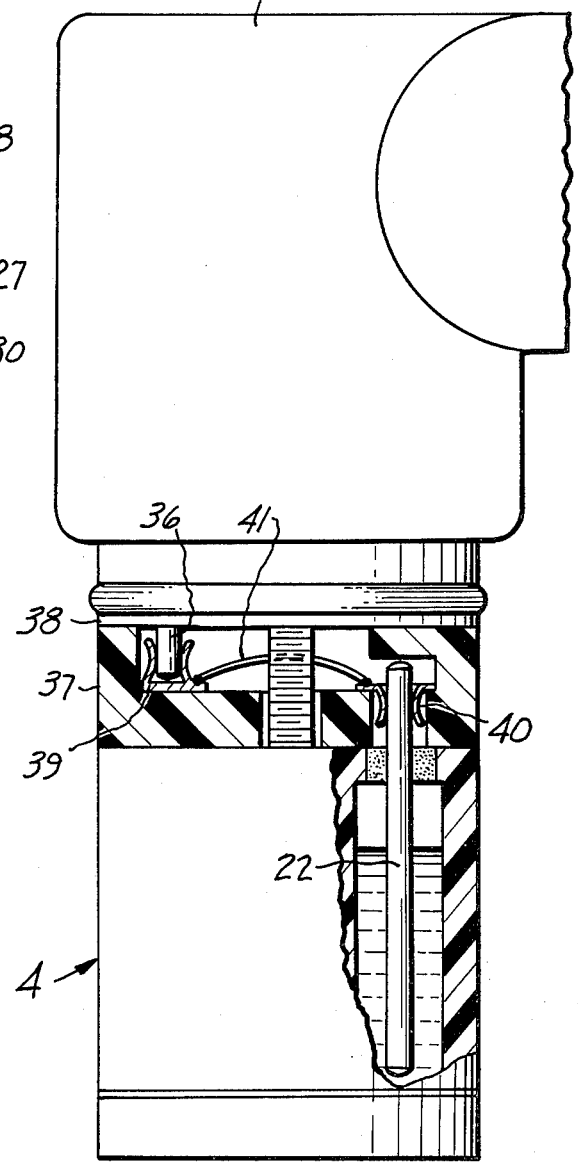
FIG. 4 shows the same sealed electrolyte housing coupled to the reusable connector by a different spacer for use when the connector's protruding anode has been substantially shortened by severing.

FIG. 4 is a modified coupling structure between the electrolyte housing 4, which is identical to that shown in FIGS. 1-3. In this modification, the reusable connector 35 has had its anode severed by the end user until it is a stub 36 which is substantially shorter than anode 26 of FIG. 3. A much smaller spacer 37 can be used between a gasket 38 and housing 4. Here spring clip sockets 39 and 40 are joined by wire 41 so that anode stub 36 and anode 22 of the electrolyte housing are in electrical contact.

In the above description, specific examples have been used to describe the invention. However, those skilled in the art will understand how to make certain modifications to these examples without departing from the spirit and scope of the invention.

I claim:

1. A sensing probe having a disposable electrolyte housing coupled to a reusable connector, which connector has a pair of electrical leads, wherein the improvement comprises: a sealed housing containing an electrolyte and two electrodes both of which are in contact with the same electrolyte; said housing including a one-piece molded thermoplastic body member that includes an outer peripheral wall, integral top wall, and an integral post depending from this top wall; said integral post having an integral closed bottom wall through which extends an electrical conductor; said post having a cavity extending downwardly from the body member's top wall; a threaded socket secured in the post's cavity; a membrane supporting cap sealing off a bottom opening of the housing, whereby the housing can be turned upside down and filled through its bottom opening prior to assembling the bottom cap, and no electrolyte can leak into the post cavity because of the integral end wall of the post; two noncoaxial conductors which extend through a wall of the sealed housing and connect to the electrodes; and noncoaxial make and break electrical contact joints between each conductor and its corresponding electrical lead on the connector, whereby the contact joints prevent rotational movement of the disposable housing relative to the reusable connector.

2. A sensing probe as set forth in claim 1, wherein the housing has a gas sensing port closed by a selectively permeable membrane, and one electrode is in close proximity to this membrane.

3. A sensing probe as set forth in claim 1, wherein the housing includes an external protruding stub in contact with one electrode through the housing wall.

4. A sensing probe as set forth in claim 3, wherein the stub is an extension of such electrode.

5. A sensing probe as set forth in claim 4, wherein there is an adhesive seal joining the housing and at least one electrode.

6. A sensing probe as set forth in claim 3, wherein the connector has a conductive socket for receiving the protruding stub.

7. A sensing probe as set forth in claim 1, wherein the housing includes a conductive threaded socket embedded in a wall of the housing, and one of the electrodes is coupled to this socket.

8. A sensing probe as set forth in claim 1, wherein the housing is thermoplastic.

9. A sensing probe as set forth in claim 1, wherein the sensing probe has a protruding O-ring for sealing the probe in a tube.

10. A disposable electrolyte housing for a sensing probe comprising: a sealed housing containing an electrolyte and two electrodes both of which are in contact with the same electrolyte; said housing including a one-piece molded thermoplastic body member that includes an outer peripheral wall, integral top wall, and an integral post depending from this top wall; said integral post having an integral closed bottom wall through which extends an electrical conductor; said post having a cavity extending downwardly from the body member's top wall; a threaded socket secured in the post's cavity; a membrane supporting cap sealing off a bottom opening of the housing, whereby the housing can be turned upside down and filled through its bottom opening prior to assembling the bottom cap, and no electrolyte can leak into the post cavity because of the integral end wall of the post; two noncoaxial conductors which extend through a wall of the sealed housing and connect to the electrodes; said conductors having noncoaxial make and break electrical coupling means adapted to prevent rotational movement of the disposable housing when coupled to a reusable connector.

11. A disposable electrolyte housing as set forth in claim 10, wherein the housing has a gas sensing port closed by a selectively permeable membrane, and one electrode is in close proximity to this membrane.

12. A disposable electrolyte housing as set forth in claim 10, wherein the housing includes an external protruding stub in contact with one electrode through the housing wall.

13. A disposable electrolyte housng as set forth in claim 12, wherein the stub is an extension of such electrode.

14. A disposable electrolyte housing as set forth in claim 13, wherein there is an adhesive seal joining the housing and at least one electrode.

15. A disposable electrolyte housing as set forth in claim 10, wherein the housing includes a conductive threaded socket embedded in a wall of the housing, and one of the electrodes is coupled to this socket.

16. A disposable electrolyte housing as set forth in claim 10, wherein the housing is thermoplastic.

17. A sensing probe having a disposable electrolyte housing coupled to a reusable connector, which connector has a pair of electrical leads, wherein the improvement comprises: a sealed housing containing an electrolyte and two electrodes both of which are in contact with the same electrolyte; two noncoaxial conductors which extend through a wall of the sealed housing and connect to the electrodes; noncoaxial make and break electrical contact joints between each conductor and its corresponding electrical lead on the connector, whereby the contact joints prevent rotational movement of the disposable housing relative to the reusable connector; and a spacer located between the connector and housing with the connector and housing each having protruding stubs, and the spacer includes coupled conductive sockets for receiving the protruding stubs.

18. A sensing probe as set forth in claim 17, wherein the sockets are offset from each other so the stubs are not coaxial.

19. A sensing probe as set forth in claim 17, wherein the reusable connector stub is substantially longer than the disposable housing stub.

20. A sensing probe as set forth in claim 17, wherein the spacer is hollow.

21. A sensing probe having a disposable electrolyte housing coupled to a reusable connector, wherein the improvement comprises: a sealed housing containing an electrolyte and two electrodes both of which are in contact with the same electrolyte; said housing including a one-piece molded thermoplastic body member that includes an outer peripheral wall, integral top wall, and an integral post depending from this wall; said integral post having an integral closed bottom wall through which extends an electrical conductor; said post having a cavity extending downwardly from the body member's top wall; a threaded socket secured in the post's cavity; a membrane supporting cap sealing off a bottom opening of the housing, whereby the housing can be turned upside down and filled through its bottom opening prior to assembling the bottom cap, and no electrolyte can leak into the post cavity because of the integral end wall of the post; two conductors which extend through a wall of the sealed housing and connect to the electrodes; and means on the sensing probe preventing rotational movement of the disposable housing relative to the reusable connector.

22. A sensing probe as set forth in claim 21, wherein the means includes a threaded screw connector grippingly securing the housing and connector together.

23. A sensing probe as set forth in claim 22, wherein the threaded screw connector is electrically coupled to one electrode.

* * * * *